US006790826B2

(12) United States Patent
Kirkness et al.

(10) Patent No.: US 6,790,826 B2
(45) Date of Patent: Sep. 14, 2004

(54) HUMAN HAEMOPOIETIC MATURATION FACTOR

(75) Inventors: Ewen F. Kirkness, Olney, MD (US); Mark D. Adams, Rockville, MD (US); Henrik Olsen, Gaithersburg, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 81 days.

(21) Appl. No.: 10/004,832

(22) Filed: Dec. 7, 2001

(65) Prior Publication Data

US 2002/0146408 A1 Oct. 10, 2002

Related U.S. Application Data

(60) Division of application No. 09/333,033, filed on Jun. 15, 1999, now Pat. No. 6,346,246, which is a division of application No. 08/442,497, filed on May 16, 1995, now Pat. No. 5,986,069, which is a continuation-in-part of application No. 08/187,186, filed on Jan. 25, 1994, now Pat. No. 5,922,572.

(51) Int. Cl.[7] .......................... A61K 38/16; A61K 38/18
(52) U.S. Cl. ................................ 514/2; 514/8; 514/12; 424/85.1; 435/325; 435/377
(58) Field of Search .................. 514/2, 8, 12; 424/85.1; 435/325, 377

(56) References Cited

U.S. PATENT DOCUMENTS

| 5,270,452 A | 12/1993 | Lim et al. |
| 5,922,572 A | 7/1999 | Rosen et al. |
| 5,986,069 A | 11/1999 | Kirkness et al. |
| 6,346,246 B1 | 2/2002 | Kirkness et al. |

FOREIGN PATENT DOCUMENTS

| EP | 92102385.9 | 3/1992 |
| EP | 0503297 A1 | 9/1992 |
| WO | WO 91/16915 | 11/1991 |
| WO | WO 92/06712 | 4/1992 |

OTHER PUBLICATIONS

Bosch et al., "Axonal signals regulate expression of glia maturation factor beta in Schwann cells; an immunohistochemical study of injured sciatic nerves and cultured Schwann cells," The Journal of Neuroscience, 9(10):3690–3698 (1989).
Bowie et al., "Deciphering the message in protein sequences: tolerance to amino acid substitutions," Science, 247:1306–1310 (1990).
Kaplan et al., "Molecular cloning and expression of biologically active human glia maturation factor–beta," Journal of Neurochemistry, 57:483–490 (1991).
Keles et al., "Expression of glia fibrillary acidic protein in human medulloblastoma cells treated with recombinant glia maturation factor beta," Oncology Research, 4(10):431–437 (1992).
Lim et al., "Antiproliferative function of glia maturation factor beta," Cell Regulation, 1:741–746 (1990).
Lim et al., "Cell–surface expression of glia maturation factor beta in astrocytes," The FASEB Journal, 4:3360–3363 (1990).
Lim et al., "Glia maturation factor beta regulates the growth of N18 neuroblastoma cells," Developmental Biology, 137:444–450 (1989).
Lim et al., "Purification and characterization of glia maturation factor beta: a growth regulator for neurons and glia," Proc. Natl. Acad. Sci. USA, 86:3901–3905 (1989).
Lim et al., "Sequential interaction of glia maturation factor with insulin," Science, 1419–1420 (1984).
Lim et al., "Structure and function of glia maturation factor beta," Plasticity and Regeneration of the Nervous System, 161–164 (1991).
Ngo et al., "Computational complexity, protein structure prediction, and the Levinthal paradox," The Protein Folding Problem and Tertiary Structure Prediction, Merz et al., eds., Birkhauser, Boston, 491–5 (1994).
Nietro–Sampedro et al., "Early release of glia maturation factor and acidic fibroblast growth factor after rat brain injury," Neuroscience Letters, 86:361–365 (1988).
Zaheer A. et al., "Expression of glia maturation factor beta mRNA and protein in rat organs and cells," J. of Neurochem., 60(3):914–920 (1993).
George et al., "Current methods in sequence comparison and analysis," Macromolecular Sequencing and Synthesis: Selected Methods and Applications, D.H. Schlesinger, ed. Alan R. Liss, Inc. NY, 127–149 (1988).
Lim et al., "Complete amino acid sequence of bovine glia maturation factor beta," Proc. Natl. Acad. Sci. USA, 7:5233–5237 (1990).
Lim et al., "Glia maturation factor–beta promotes the appearance of large neurofilament–rich neurons in injured rat brains," Brain Research, 504:154–158 (1989).
Wang et al., "Polyclonal antibody localizes glia maturation factor beta–like immunoreactivity in neurons and glia," Brain Research, 591:1–7 (1992).

(List continued on next page.)

*Primary Examiner*—Elizabeth Kemmerer
(74) *Attorney, Agent, or Firm*—Human Genome Sciences, Inc.

(57) ABSTRACT

Disclosed are human haemopoietic maturation factor polypeptides and DNA (RNA) encoding such haemopoietic maturation factor polypeptides. Also provided are procedures for producing such polypeptides by recombinant techniques and for using such polypeptides for treating leukemia, auto-immune diseases and blood related disorders. Antagonists against such polypeptides and their use as a therapeutic to prevent expansion of T-cell populations are also disclosed. Diagnostic assays are also disclosed to detect both the presence of mutations in the haemopoietic maturation factor nucleic acid sequences and altered levels of the protein.

40 Claims, 8 Drawing Sheets

OTHER PUBLICATIONS

Genbank Accession No. T65874 (Feb. 21, 1995).
Genbank Acession No. AA297829 (Apr. 18, 1997).
Genbank Accession No. T66033 (Feb. 21, 1995).
Genbank Accession No. T51240 (Feb. 6, 1995).
Genbank Accession No. AA297559 (Apr. 18, 1997).
Genbank Accession No. AA297558 (Apr. 18, 1997).
Genbank Accession No. T51355 (Feb. 6, 1995).
Genbank Accession No. Z11558 (Feb. 10, 1999).
Genbank Accession No. M86492 (Dec. 31, 1994).
Genbank Accession No. S22149 (Jun. 16, 2000).
Genbank Accession No. PT0410 (Sep. 29, 1999).
Geneseq Accession No. R43941 (Jun. 10, 1994).
Geneseq Accession No. T19749 (Jul. 11, 1996).
Geneseq Accession No. Q53862 (Jun. 10, 1994).

FIG. 1A

```
      AGACAGCGGAACTAAGAAAGAAGAGGCCTGTGGACAGAACAATCATGTCTGACTCCCTG
  1   ------+---------+---------+---------+---------+---------+  60
                                                   MetSerAspSerLeu

GTGGTGTGCGAGGTAGACCCAGAGCTAACAGAAAAGCTGAGGAAATTCCGCTTCCGAAAA
 61   ------+---------+---------+---------+---------+---------+  120
      ValValCysGluValAspProGluLeuThrGluLysLeuArgLysPheArgLys

GAGACAGACAATGCAGCCATCATAATGAAGGTGGACAAAGACCGGCAGATGGTGGTGCTG
121   ------+---------+---------+---------+---------+---------+  180
      GluThrAspAsnAlaAlaIleIleMetLysValAspLysAspArgGlnMetValValLeu

GAGGAAGAATTTCAGAACATTTCCCCAGAGGAGCTCANAATGGAGTTGCCGGAGAGACAG
181   ------+---------+---------+---------+---------+---------+  240
      GluGluGluPheGlnAsnIleSerProGluGluLeuLysMetGluLeuProGluArgGln

CCCAGGTTCGTGGTTACAGCTACAAGTACTACAAGTACGTGCATGACGATGGCCGAGTGTCCTACCCT
241   ------+---------+---------+---------+---------+---------+  300
      ProArgPheValValTyrSerTyrLysTyrValHisAspAspGlyArgValSerTyrPro
```

FIG. 1B

```
     TTGTGTTTCATCTTCTCCAGCCCTGTGGGCTGCAAGCCGGAACAACAGATGATGTATGCA
301  ------+---------+---------+---------+---------+---------+ 360
     LeuCysPheIlePheSerSerProValGlyCysLysProGluGlnMetMetTyrAla

GGGAGTAAAAACAGGCTGGTGCAGACAGCAGAGCTCACAAAGGTGTTCGAAATCCGCACC
361  ------+---------+---------+---------+---------+---------+ 420
     GlySerLysAsnArgLeuValGlnThrAlaGluLeuThrLysValPheGluIleArgThr

ACTGATGACCTCACTGAGGCCTGGCTCCAAGAAAAGTTGTCTTTCTTTCGTTGATCTCTG
421  ------+---------+---------+---------+---------+---------+ 480
     ThrAspAspLeuThrGluAlaTrpLeuGlnGluLysLeuSerPhePheArg

GGCTGGGGACTGAATTCCCTGATGTCTGAGTCCTCAAGGTGACTGGGGACTTGGAACCCT
481  ------+---------+---------+---------+---------+---------+ 540

AGGACCTGAACAACCAAGACTTTAAATAAATTTTAAATGCAAAAAAAAAAAAAAAAAAA
541  ------+---------+---------+---------+---------+---------+ 600
```

FIG. 2

```
Query:  46  MSDSLVVCEVDPELTEKLRKFRFRKETDNAAIIMKVDKDRQMVVLEEFQNISPEELKME  225
            MS+SLVVC+V  +L EKLRKFRFRKET+NAAIIMK+DKD+++VVL+EE + ISP+ELK E
Sbjct:   1  MSESLVVCDVAEDLVEKLRKFRFRKETNNAAIIMKIDKDKRLVVLDEELEGISPDELKDE   60

Query: 226  LPERQPRFVVYSYKYVHDDGRVSYPLCFIFSSPVGCKPEQQMMYAGSKNRLVQTAELTKV  405
            LPERQPRF+VYSYKY HDDGRVSYPLCFIFSSPVGCKPEQQMMYAGSKN+LVQTAELTKV
Sbjct:  61  LPERQPRFIVYSYKYQHDDGRVSYPLCFIFSSPVGCKPEQQMMYAGSKNKLVQTAELTKV  120

Query: 406  FEIRTTDDLTEAWLQEKLSFF  468
            FEIR T+DLTE WL+EKL FF
Sbjct: 121  FEIRNTEDLTEEWLREKLGFF  141
```

HUMAN HAEMOPOIETIC MATURATION FACTOR

CROSS REFERENCE TO RELATED APPLICATIONS

This application is a divisional of and claims priority under 35 U.S.C. §120 to U.S. application Ser. No. 09/333,033, filed Jun. 15, 1999 now U.S. Pat. No. 6,346,246, which is a divisional of and claims priority under 35 U.S.C. §120 to U.S. application Ser. No. 08/442,497, filed May 16, 1995 (now U.S. Pat. No. 5,986,069, issued on Nov. 16, 1999), which is a continuation in part of and claims priority under 35 U.S.C. §120 to U.S. application Ser. No. 08/187,186 filed Jan. 25, 1994 (now U.S. Pat. No. 5,922,572, issued on Jul. 13, 1999), all of which are incorporated herein in their entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. The polypeptides of the present invention have been putatively identified as a human haemopoietic maturation factor, sometimes hereinafter referred to as "HMF". The invention also relates to inhibiting the action of such polypeptides.

BACKGROUND OF THE INVENTION

Various growth factors have been discovered, studied and utilized (cellular and molecular biology, edited by the Japanese Tissue Culture Association, Asakura Shoten (1987). Such cell growth factors include epidermal growth factor, platelet derived growth factor, acidic fibroblast growth factor and basic fibroblast growth factor among others. All these factors have been isolated based upon growth promotion of fibroblast cells. However, these factors have also been found to display widely ranging activity and poor specificity.

Accordingly, recent attempts have been made to search for growth factors specifically acting on functionally differentiated cells. As a result, growth factors such as keratinocyte growth factor and hepatocyte growth factor have been isolated, thus creating the possibility that these factors could be used to treat diseases vulnerable to their specific action spectra. Another growth factor which has been isolated is disclosed in European Patent Application No. 92102385.9 applied for by Takeda Chemical Industries, Ltd. disclosing a glia activating factor which has glial cell growth promoting activity, and the DNA encoding for that polypeptide.

Hematopoiesis is the production of blood cells. The major hematopoietic tissues are bone marrow, spleen, lymph nodes and thymus. Hematopoiesis in the human embryo begins in the second week of life. Bone marrow appears in the embryo in the second month, and it becomes the dominant hematopoietic organ in the latter half of gestation and throughout postnatal life. The bone marrow contains stem cells that give rise to all cells of the haemopoietic series. All of the blood cells except T-lymphocytes are produced in the marrow.

SUMMARY OF THE INVENTION

The polypeptides of the present invention has been putatively identified as a haemopoietic maturation factor polypeptide based on amino acid sequence homology to Human glia maturation factor polypeptides.

In accordance with one aspect of the present invention, there are provided novel polypeptides, as well as biologically and diagnostically active fragments, analogs and derivatives thereof. The polypeptides of the present invention is of human origin.

In accordance with another aspect of the present invention, there are provided isolated nucleic acid molecules encoding such polypeptides, including mRNAs, DNAs, cDNAs, genomic DNA, as well as biologically active and diagnostically or therapeutically useful fragments, analogs and derivatives thereof.

In accordance with still another aspect of the present invention, there are provided procedures for producing such polypeptides by recombinant techniques comprising culturing recombinant prokaryotic and/or eukaryotic host cells, containing a nucleic acid sequence encoding the polypeptide of the present invention, under conditions promoting expression of said protein and recovery of said protein.

In accordance with yet a further aspect of the present invention, there are also provided nucleic acid probes comprising nucleic acid molecules of sufficient length to specifically hybridize to the nucleic acid sequences of the present invention.

In accordance with yet a further aspect of the present invention, there is provided a process for utilizing such polypeptides, or polynucleotide encoding such polypeptide, for therapeutic purposes, for example, to treat leukemia, blood related disorders, to stimulate differentiation and proliferation of cells of hematopoietic or stromal origin, and to remove malignant cells.

In accordance with yet another aspect of the present invention, there are provided antibodies against such polypeptides.

In accordance with yet another aspect of the present invention, there are provided antagonists against such polypeptides, which may be used to inhibit the action of such polypeptides, for example, to treat auto-immune diseases by preventing expansion of certain T-cell populations.

In accordance with still another aspect of the present invention, there are provided diagnostic assays for detecting diseases or susceptibility to diseases related to mutations in the nucleic acid sequences and altered levels of the polypeptides of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are meant only as illustrations of specific embodiments of the present invention and are not meant as limitations in any manner.

FIGS. 1A–B illustrate the cDNA sequence (SEQ ID NO:1) and corresponding deduced amino acid sequence (SEQ ID NO:2) of the polypeptide of the present invention. The standard three letter abbreviation has been used to depict the amino acid sequence. Sequencing was performed using a 373 Automated DNA sequencer (Applied Biosystems, Inc.). Sequencing accuracy is predicted to be greater than 97% accurate.

FIG. 2 shows the amino acid sequence homology between the polypeptide of the present invention (top line; SEQ ID NO:2) and glia maturation factor β (bottom line; SEQ ID NO:9).

DETAILED DESCRIPTION OF THE INVENTION

Figure 3:
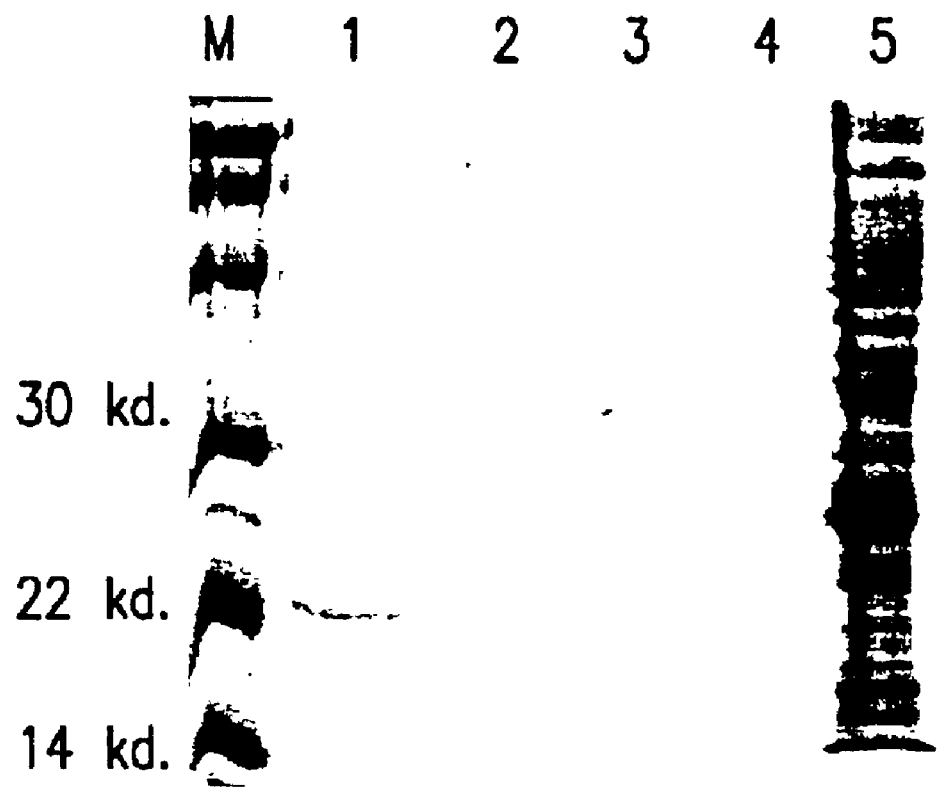
FIG. 3 illustrates a gel wherein a purified polypeptide of the present invention has been electrophoresed after bacterial expression and purification.
Figure 4A:
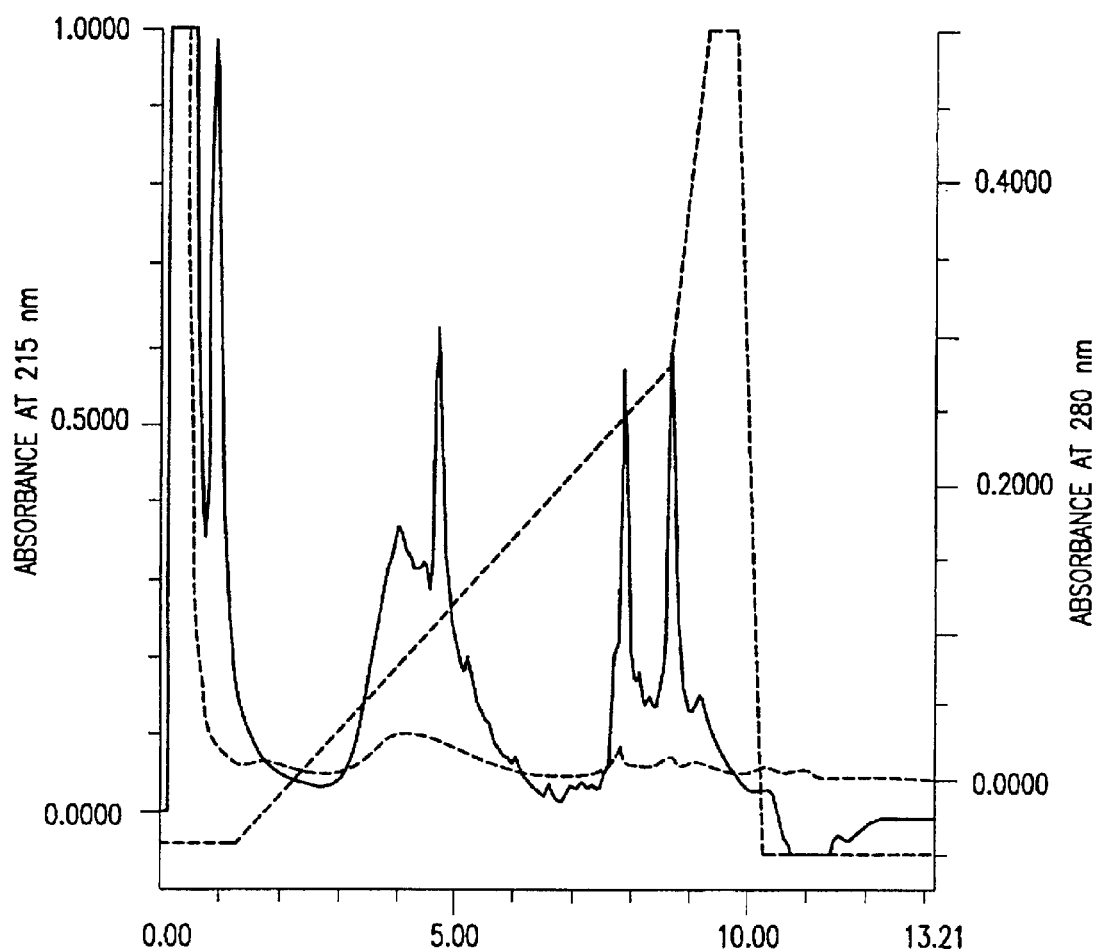
FIG. 4A is a reverse-phase HPLC analysis of haemopoietic maturation factor expression media after expression in baculovirus.
Figure 4B:
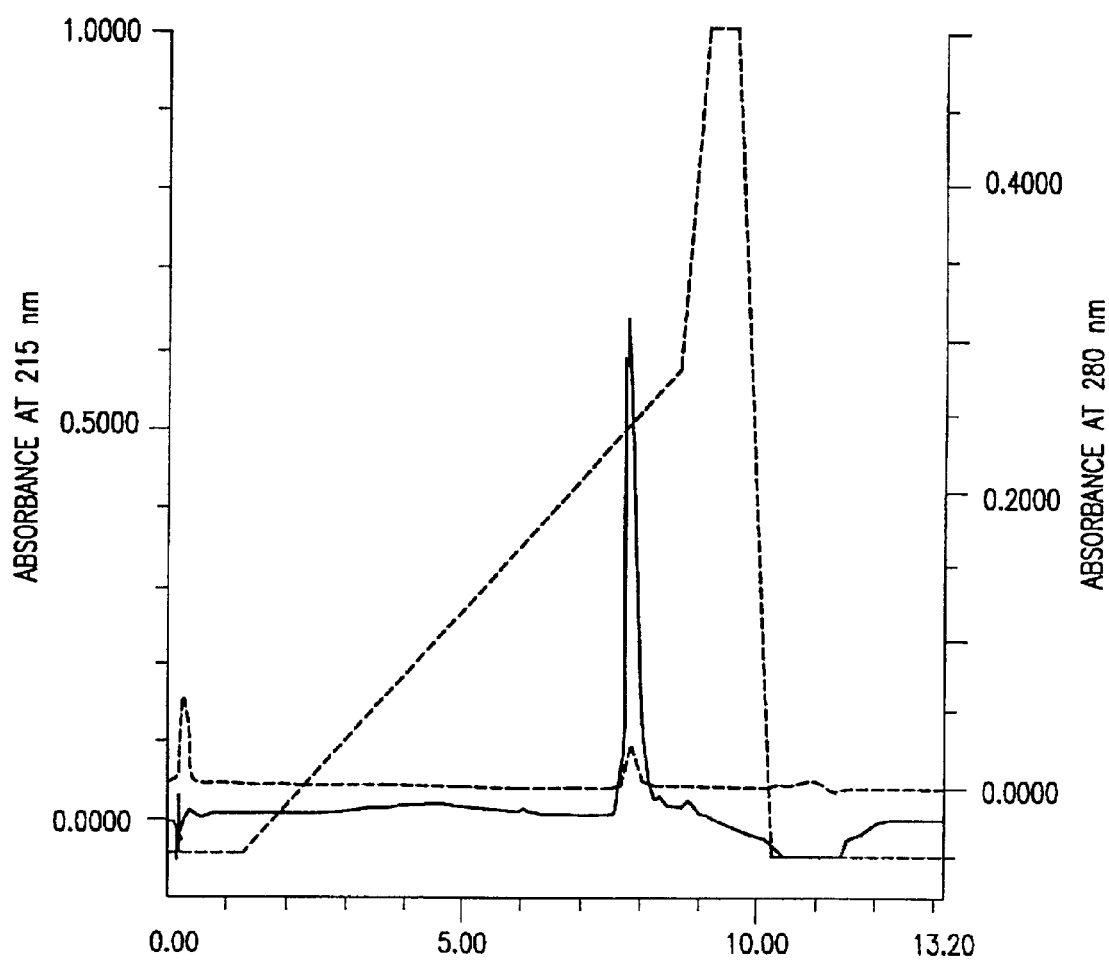
FIG. 4B is a reverse-phase HPLC analysis of haemopoietic maturation factor expression media after expression and purification in baculovirus.

In accordance with an aspect of the present invention, there are provided isolated nucleic acids (polynucleotide) which encode for the mature polypeptide having the deduced amino acid sequence of FIGS. 1A–B (SEQ ID NO:2) or for the mature polypeptide encoded by the cDNA of the clone deposited with the American Type Culture Collection (ATCC), 10801 University Boulevard. Manassas, Va. 20110-2209 (present address), as ATCC Deposit No. 75514 on Aug. 4, 1993. Since the deposit is being maintained under the terms of the Budapest Treaty, it will be made available to a patent office signatory to the Budapest Treaty.

A polynucleotide encoding a polypeptide of the present invention may be obtained from a cDNA library derived from human early stage kidney, spleen and thymus tissues. It contains an open reading frame encoding a protein of 142 amino acid residues. The protein exhibits the highest degree of homology to human and bovine glia maturation factor with 82% identity and 92% similarity over the entire coding sequence.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–B (SEQ ID NO:1) or that of the deposited clone or may be a different coding sequence which coding sequence, as a result of the redundancy or degeneracy of the genetic code, encodes the same mature polypeptide as the DNA of FIGS. 1A–B (SEQ ID NO:1) or the deposited cDNA.

The polynucleotide which encodes for the mature polypeptide of FIGS. 1A–B (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The term "gene" means the segment of DNA involved in producing a polypeptide chain; it includes regions preceding and following the coding region (leader and trailer) as well as intervening sequences (introns) between individual coding segments (exons).

The present invention further relates to variants of the hereinabove described polynucleotides which encode for fragments, analogs and derivatives of the polypeptide having the deduced amino acid sequence of FIGS. 1A–B (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–B (SEQ ID NO:2) or the same mature polypeptide encoded by the cDNA of the deposited clone as well as variants of such polynucleotides which variants encode for a fragment, derivative or analog of the polypeptide of FIGS. 1A–B (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–B (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIGS. 1A–B (SEQ ID NO:1) or the deposited cDNA.

Alternatively, the polynucleotide may be a polynucleotide that has at least 20 bases, preferably at least 30 bases and more preferably at least 50 bases which hybridize to a polynucleotide of the present invention and which has an identity thereto as hereinabove described and which encodes a polypeptide which does not retain activity. Such polynucleotides may be employed as probes for the polynucleotide of SEQ ID NO:1 for example, for recovering the polynucleotide or as a diagnostic probe, or as a PCR primer.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIGS. 1A–B (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–B (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–B (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence or (v) one in which the polypeptide is an active fragment of the full-length polypeptide which has less than all the amino acid residues of the polypeptide shown in FIGS. 1A–B (SEQ ID NO:2), but still retains biological activity. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the HMF genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli*, Streptomynes, *Salmonella typhimurium*; fungal cells, such as yeast; insect cells such as Drosophila S2 and Spodoptera Sf9; animal cells such as CHO, COS or *Bowes melanoma*; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacd, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Fragments of the polypeptides of the present invention may be employed for producing the corresponding full-length polypeptide by peptide synthesis, therefore, the fragments may be employed as intermediates for producing the full-length polypeptides. Fragments of the polynucleotides of the present invention may be used in a similar manner to synthesize the full-length polynucleotides of the present invention.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation, initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillis subtilis, Salmonella typhimumrium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis. USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Figure 5:
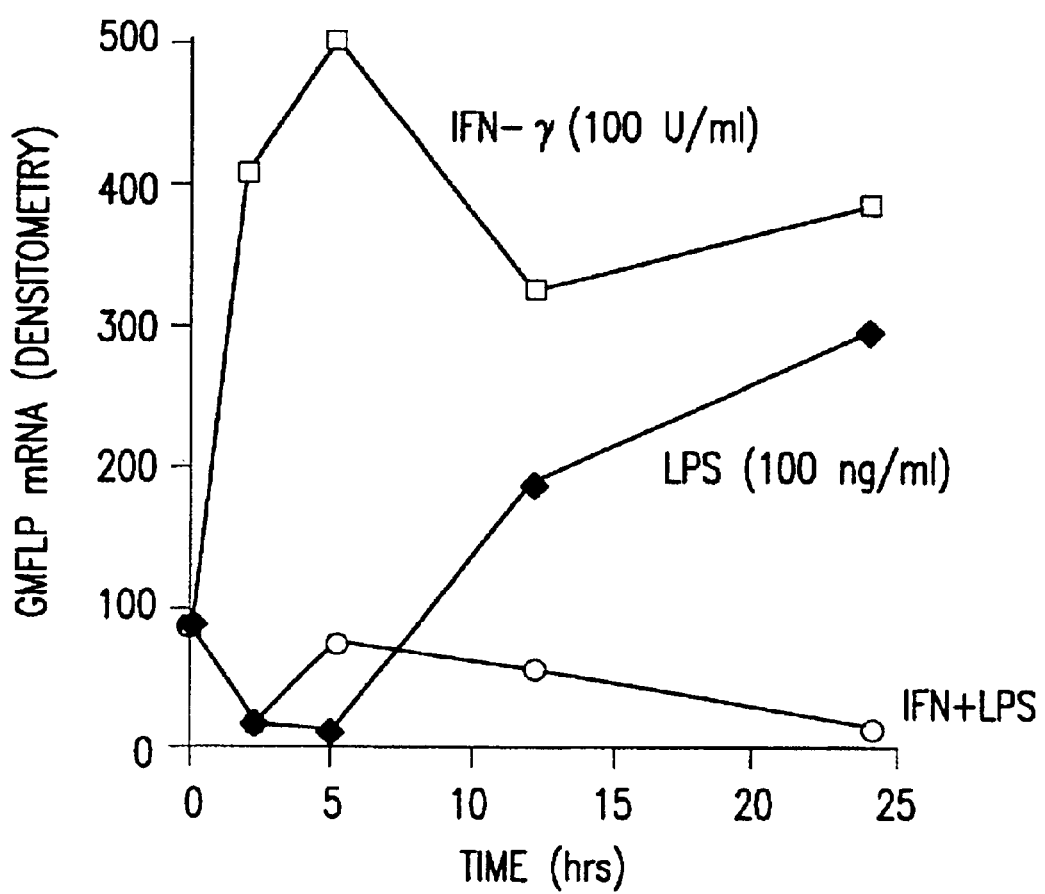
FIG. 5 is a graph illustrating the expression level of mRNA encoding haemopoietic maturation factor in human monocytes treated with recombinant interferon-gamma (IFN-γ), LPS, or both stimuli. The bands on the resulting autoradiograph were quantified densitometrically.
Figure 6A:
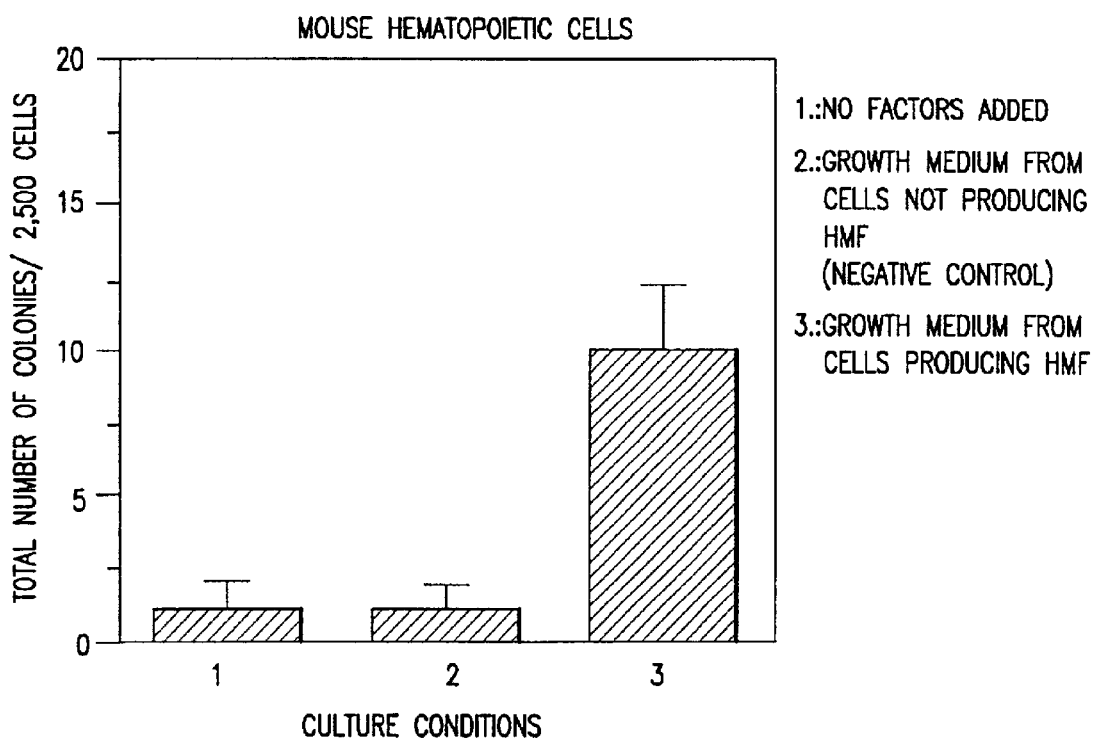
FIGS. 6A and B illustrate that HMF stimulates the formation of haemopoietic progenitor cell colonies from mouse (6A) and human (6B) bone marrow cells. 6A, part 1, No factors added; 6A, part 2, growth medium from cells not producing HMF (negative control); 6A, part 3, growth medium from cells producing HMF. 6B, part 1, No factors added; 6B, part 2, column fraction not containing HMF; 6B, part 3, partially purified HMF.
Figure 6B:
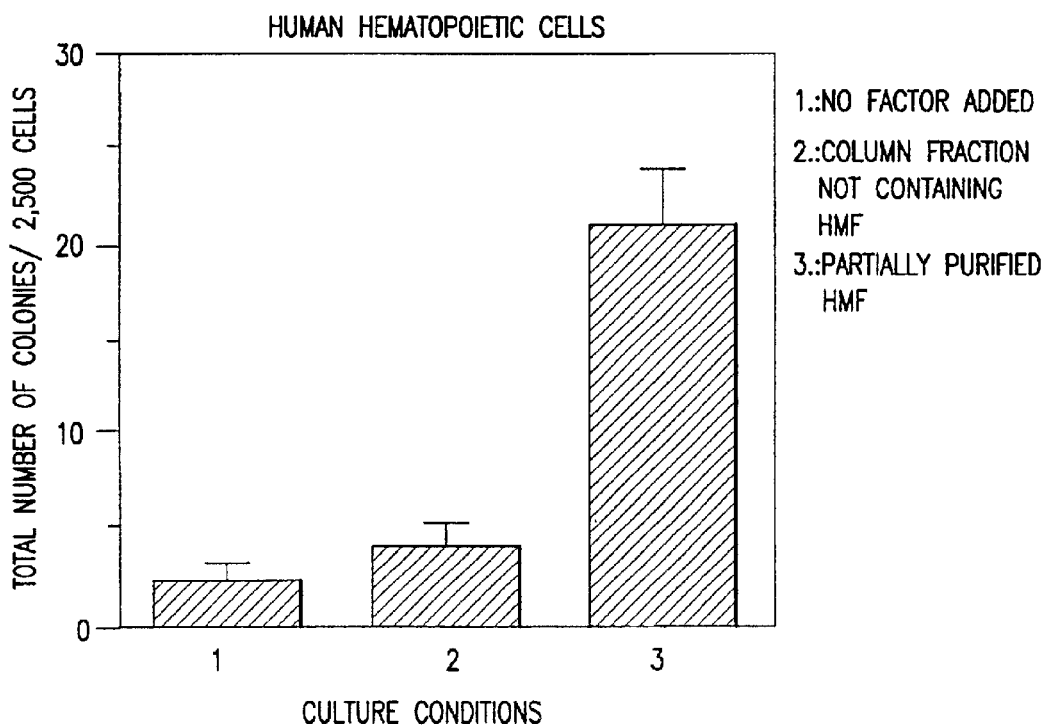

Leukemia is clinically featured by suppression of normal blood cell formation resulting from suppression of normal haemopoiesis by factors produced by leukemic cells. This results in anemia, thrombocytopenia and granulocytopenia. The polypeptide of the present invention is expressed in human monocytes at the mRNA level as shown in FIG. 5, indicating a role in stimulation of haemopoiesis. Further, the polypeptide of the present invention is shown to significantly stimulate haemopoiesis, Example 5, by causing proliferation and differentiation of mouse and human bone marrow cells as shown in FIGS. 6A–B.

Accordingly, administration of a therapeutically effective amount of the polypeptide of the present invention may be employed to overcome the suppression of haemopoiesis by leukemic cells. The polypeptide of the present invention may also be employed for treating other blood related disorders, e.g., hemolysis, polycythemia vera, melogibrosis, hemophilia, and splenomegaly.

The polypeptide of the present invention acts to stimulate differentiation of immature malignant leukemia cells thereby removing the immature malignant cell population.

For example, the polynucleotide of the present invention has been shown to inhibit HeLa cell growth, as shown in the following table. HeLa cells are cancer cells, for example malignant leukemic cells (See Example 2).

| Haemopoietic maturation factor and HeLa cell growth. | | | |
|---|---|---|---|
| Experiment # Cell Number | Exp. 1 ($\times 10^5$; SD) [% cntl] | Exp. 2 ($\times 10^4$; SD) [% cntl] | Exp. 3 ($\times 10^4$; SD) [% cntl] |
| Haemopoietic maturation factor ($\mu$g/ml). | | | |
| 0 | 3.2; 0.2 | 6.0; 0.3 | 5.1; 0.3 |
| 0.1 | 2.9; 0.3 [91] | 6.0; 0.3 [100] | 4.6; 0.3 [90] |
| 1.0 | 2.9; 0.3 [91] | 4.2; 0.3 [70] | 4.4; 0.5 [86] |
| 10.0 | 1.5; 0.2 [47] | 3.7; 0.6 [62] | 2.3; 0.2 [45] |

SD; standard deviation
[% cntl]; percent cells compared to untreated 0$\mu$g/ml haemopoietic maturation factor.

The polypeptide of the present invention may also be employed to offset the destruction of haemopoietic cell precursors which occurs during radiation or chemotherapy.

The polypeptide of the present invention may also be employed to proliferate stromal cell differentiation by causing the expansion of the stromal cell population and the subsequent expansion of haemopoietic cells.

The polypeptide of the present invention may be employed to stimulate the differentiation of mature blood cells in situations where a patient has undergone a bone marrow transplant, for example, in the case of cancer.

The polypeptide of the present invention may also be employed to stimulate bone marrow/haemopoietic cells in vitro for gene therapy purposes and for stimulation of bone marrow recovery due to chemotherapy, as shown in Example 6 and depicted in FIG. 7.

The polypeptide of the present invention may be employed to stimulate the proliferation and differentiation of certain human T-cell populations and treat diseases of T-cell deficiencies, for example leukemia, HIV infection. HIV infection results in suppression of the differentiation of T-cell populations. Purified polypeptides of the present invention were assayed for their biological effect on human peripheral T cells. Total (mixed CD4+ and CD8+ subsets) T cells were induced to proliferate between 3- and 6-fold when incubated in the presence of 3–25 ng/ml of pure protein. Separation of the cells into the CD4+ and CD8+ subsets prior to stimulation revealed that the CD4+ subset is primarily responsive to the polypeptides of the present invention, showing 10-fold and greater levels of proliferation (see Example 7). Notably, stimulation of T cells with the polypeptides of the present invention is achieved in the absence of a co-signal i.e., lectin or PMA. The results are shown in Table 1 below.

TABLE 1

| Haemopoietic Maturation Factor | mean | sd | n | sem | stimulation index |
|---|---|---|---|---|---|
| CD4 + T cells | | | | | |
| 0.0 ng/ml | 306.25 | 130 | 4 | 47.6 | 1 |
| 0.34 ng/ml | 833.75 | 122 | 4 | 95.3 | 2.7 |
| 0.78 ng/ml | 842 | 666 | 4 | 230.8 | 2.7 |
| 1.56 ng/ml | 497 | 151 | 4 | 262 | 2.4 |
| 3.12 ng/ml | 1315 | 655 | 4 | 238 | 4.29 |
| 6.25 ng/ml | 2029 | 55 | 4 | 90.5 | 6.6 |
| 12.5 ng/ml | 1741 | 1274 | 4 | 388 | 5.6 |
| 25 ng/ml | 3128 | 948 | 4 | 963 | 10.2 |
| 50 ng/ml | 2918 | 953 | 4 | 287 | 6.59 |
| 100 ng/ml | 1642 | 234 | 4 | 377 | 5.36 |

TABLE 1-continued

| Haemopoietic Maturation Factor | mean | sd | n | sem | stimulation index |
|---|---|---|---|---|---|
| CD8 + T cells | | | | | |
| 0.0 ng/ml | 258 | 230 | 4 | 74.25 | 1 |
| 0.34 ng/ml | 511 | 127 | 3 | 130.9 | 1.98 |
| 0.78 ng/ml | 346 | 63 | 4 | 25.26 | 1.34 |
| 1.56 ng/ml | 338 | 30 | 4 | 78.3 | 1.31 |
| 3.12 ng/ml | 566 | 53 | 3 | 234.5 | 1.81 |
| 6.25 ng/ml | 498 | 110 | 4 | 35.5 | 1.93 |
| 12.5 ng/ml | 431 | 13 | 4 | 66.5 | 1.67 |
| 25 ng/ml | 782 | 640 | 4 | 202.9 | 3.03 |
| 50 ng/ml | 615 | 38 | 4 | 60.25 | 2.3 |
| 100 ng/ml | 428 | 51 | 4 | 68.5 | 1.65 |
| total T cells | | | | | |
| 0.0 ng/ml | 171 | 77 | 4 | 32.5 | 1 |
| 0.34 ng/ml | 340 | 95 | 4 | 44 | 1.98 |
| 0.78 ng/ml | 329 | 103 | 4 | 48.7 | 1.92 |
| 1.56 ng/ml | 573 | 233 | 3 | 116 | 3.35 |
| 3.12 ng/ml | 372 | 181 | 4 | 73 | 2.19 |
| 6.25 ng/ml | 427 | 282 | 4 | 90.5 | 2.49 |
| 12.5 ng/ml | 528 | 104 | 4 | 57 | 3.08 |
| 25 ng/ml | 604 | 267 | 3 | 141 | 3.5 |
| 50 ng/ml | 606 | 360 | 3 | 180 | 3.54 |
| 100 ng/ml | 1086 | 1358 | 4 | 679 | 6.35 |

Further proof that the polypeptide of the present invention is involved in T cell stimulation is the induction of the polypeptide of the present invention in response to a foreign stimulus, such as lipopolysaccharide (FIG. 5).

Thymocytes obtained from normal rats were also responsive to the polypeptide of the present invention (Table 2) in a similar dose response range. Isolated human DN thymocytes, CD4+ thymocytes and CD8+ thymocytes rigorously depleted of thymic stroma, however, did not respond to HMF (see Example 8). Thymic stroma may be involved in the stimulation of early T-cell precursors and developing thymocyte in conjunction with haemopoietic maturation factor. The results of contacting thymic cell suspensions with baculovirus expressed HMF are shown in Table 2. The first group relates to stimulation of thymocyte by HPLC purified HMF from the supernatant of cells expressing HMF. The control was performed in the absence of HMF. The supernatant corresponds to the addition to the thymocyte of supernatant containing cells which express HMF, where the HMF has not been purified. The results indicate that the supernatant does not stimulate proliferation as effectively.

TABLE 2

| | mean | sd | n | sem | stimulation index |
|---|---|---|---|---|---|
| Thymocyte; Purified HMF added | | | | | |
| 0.0 ng/ml | 403 | 64 | 4 | 32 | 1 |
| 0.34 ng/ml | 544 | 340 | 3 | 170 | 1.3 |
| 0.78 ng/ml | 725 | 208 | 4 | 105 | 1.8 |
| 1.56 ng/ml | 477 | 93 | 4 | 46.6 | 1.2 |
| 3.13 ng/ml | 1659 | 753 | 4 | 377 | 4.1 |
| 6.25 ng/ml | 1335 | 445 | 4 | 223 | 3.3 |
| 12.5 ng/ml | 1447 | 415 | 4 | 208 | 3.6 |
| 25 ng/ml | 2612 | 1877 | 4 | 939 | 6.5 |
| 50 ng/ml | 984 | 143 | 4 | 72 | 2.4 |
| 100 ng/ml | 1307 | 716 | 4 | 358 | 3.2 |
| control | | | | | |
| 0.0 ng/ml Thymocyte; | 403 | 64 | 4 | 32 | 1 |
| Supernatant added | | | | | |
| 0.34 ng/ml | 285 | 51 | 4 | 25.6 | 0.7 |
| 0.78 ng/ml | 358 | 81 | 4 | 40.8 | 0.88 |
| 1.56 ng/ml | 389 | 91 | 4 | 46 | 0.96 |
| 3.21 ng/ml | 386 | 18 | 4 | 9.2 | 0.95 |
| 6.25 ng/ml | 337 | 74 | 4 | 37 | 0.83 |
| 12.5 ng/ml | 414 | 93 | 4 | 46.9 | 1.02 |
| 25 ng/ml | 635 | 204 | 4 | 102 | 1.57 |
| 50 ng/ml | 615 | 341 | 4 | 171 | 1.5 |
| 100 ng/ml | 372 | 150 | 5 | 75.5 | 0.9 |

This invention also provides a method for identification of the receptor for the polypeptide of the present invention. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptide of the present invention, and a cDNA library created from this RNA is divided into pools and used to transfect COS cells or other cells that are not responsive to HMF. Transfected cells which are grown on glass slides are exposed to labeled HMF. HMF can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled ligand can be photoaffinity linked with cell membrane or extract preparations that express the receptor molecule. Cross-linked material is resolved by SDS-PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

The mRNA encoding the polypeptide of the present invention was found to be highly expressed in the spleen, thymus and bone marrow cells as a result of Northern Blot analysis. Northern blot analysis of the polypeptide of the present invention was performed by size fractionating Poly A+ mRNA (1 µg) from a variety of human tissues on a 1% agarose-formaldehyde gel, which were then transferred to nylon membranes (Zetabind) and hybridized under high-stringency conditions with a $^{32}$P-labeled HMF cDNA probe. Normalization was performed with a β-actin probe.

The expression of the nucleic acid sequence of the present invention in haemopoietic cells was analyzed further by isolating RNA from numerous cell lines of haemopoietic origin. Total RNA was isolated and separated by denaturing gel chromatography and the RNA (app. 10 µg by OD) was transferred to a membrane. RNA expression pattern was determined by hybridizing the membrane to a radioactive probe spanning the nucleic acid sequence followed by autoradiography. The polypeptide of the present invention is expressed in a number of haemopoietic cell and cell lines, for example, CD4−/CD8−, CD4+/CD8+, total thymus, Jurkat, MOLT3, CEM and SB, but not in thymic stromal cells. In several cases a decrease in expression was observed following maturation of haemopoietic cells. As an example, the polypeptide of the present invention is expressed to a higher level in normal peripheral T-cells, than in activated peripheral T-cells. Also a decreased level of expression is observed when CD4−/CD8− thymic T-cells, are compared to CD4+/CD8+ thymic T-cells. This indicates that the polypeptide of the present invention is primarily active in immature cells.

In accordance with yet a further aspect of the present invention, there is provided a process for utilizing such polypeptides, or polynucleotides encoding such polypeptides, as a research reagent for in vitro purposes related to scientific research, synthesis of DNA and manufacture of DNA vectors, for the purpose of developing therapeutics and diagnostics for the treatment of human disease.

Fragments of the full length HMF gene may be used as a hybridization probe for a cDNA library to isolate other genes which have a high sequence similarity to the HMF gene or similar biological activity. Probes of this type preferably, have at least 30 bases and may contain, for example, 50 bases or more. The probe may also be used to identify a cDNA clone corresponding to a full length transcript and a genomic clone or clones that contain the complete gene including regulatory and promoter regions, exons, and introns. An example of a screen comprises isolating the coding region of the HMF gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention is also directed to assays for identifying agonists and antagonists to HMF. For example, T-cells, such as CD4+ and CD8+, may be isolated by negative selection with a panning procedure using anti-CD4+ and anti-CD8+ monoclonal antibodies. The isolated cells are then contacted with the compound to be screened, HMF and pulsed with 1 $\mu$Ci of $^3$[H]-thymidine. The cpm incorporation is then determined by liquid scintillation counting and compared to control assay in the absence of the compound to determine if the compound is an effective agonist or antagonist.

Examples of potential antagonists to the polypeptide of the present invention include an antibody, or in some cases, an oligonucleotide, which binds to the polypeptide. Alternatively, a potential antagonist may be a closely related protein, for example a mutated form of HMF, which binds to the HMF receptors, but elicits no response.

Another potential HMF antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of HMF. The antisense RNA oligonucleotide hybridizes to the mRNA in vivo and blocks translation of the mRNA molecule into the HMF polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of HMF.

The antagonists may be employed to prevent expansion of certain T-cell populations which may be employed for treating conditions related to the presence of T-cells, for example graft rejection and auto-immune diseases where T cells are directed against a host's own tissues.

The HMF antagonists may also be employed to prevent the growth and differentiation of immature leukemic cells stimulated by HMF. The antagonists may be employed in a composition with a pharmaceutically acceptable carrier, e.g., as hereinafter described.

The HMF polypeptides and agonists or antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The HMF polypeptide, and agonists and antagonists which are polypeptides, may also be employed in accordance with the present invention by expression of such polypeptide in vivo, which is often referred to as "gene therapy."

Thus, for example, cells such as bone marrow cells may be transduced with a polynucleotide (DNA or RNA) encoding for the polypeptide ex vivo, the transduced cells are then provided to a patient to be treated with the polypeptide. Such methods are well-known in the art. For example, cells may be transduced by procedures known in the art by use of a retroviral particle containing RNA encoding for the polypeptide of the present invention.

Similarly, transduction of cells may be accomplished in vivo for expression of the polypeptide in vivo, for example, by procedures known in the art. As known in the art, a producer cell for producing a retroviral particle containing RNA encoding the polypeptide of the present invention may be administered to a patient for transduction in vivo and expression of the polypeptide in vivo.

These and other methods for administering a polypeptide of the present invention by such methods should be apparent to those skilled in the art from the teachings of the present invention. For example, the expression vehicle for transducing cells may be other than a retroviral particle, for example, an adenovirus, which may be used to transduce cells in vivo after combination with a suitable delivery vehicle.

The retroviral plasmid vectors may be derived from retroviruses which include, but are not limited to, Moloney Murine Sarcoma Virus, Moloney Murine Leukemia Virus, spleen necrosis virus, Rous Sarcoma Virus and Harvey Sarcoma Virus. In a preferred embodiment the retroviral expression vector, pMV-7, is flanked by the long terminal repeats (LTRs) of the Moloney murine sarcoma virus and contains the selectable drug resistance gene neo under the regulation of the herpes simplex virus (HSV) thymidine kinase (tk) promoter. Unique EcoRI and HindIII sites facilitate the introduction of coding sequence (Kirschmeier, P. T. et al., DNA, 7:219–25 (1988)).

The vectors include one or more suitable promoters which include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). The selection of a suitable promoter will be apparent to those skilled in the art from the teachings contained herein.

The nucleic acid sequence encoding the polypeptide of the present invention is under the control of a suitable promoter which includes, but is not limited to, viral thymidine kinase promoters, such as the Herpes Simplex thymidine kinase promoter; retroviral LTRs, the β-actin promoter, and the native promoter which controls the gene encoding the polypeptide.

The retroviral plasmid vector is employed to transduce packaging cell lines to form producer cell lines. Examples of packaging cells which may be transfected include, but are not limited to, the PE501, PA317 and GP+am12. The vector may transduce the packaging cells through any means known in the art. Such means include, but are not limited to, electroporation, the use of liposomes, and CaPO$_4$ precipitation.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced, include but are not limited to, fibroblasts and endothelial cells.

This invention is also related to the use of the HMF gene as a diagnostic. Detection of a mutated form of the gene of the present invention will allow a diagnosis of a disease or a susceptibility to a disease which results from underexpression of HMF for example, leukemia.

Individuals carrying mutations in the gene of the present invention may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding HMF can be used to identify and analyze HMF mutations. For example, deletions and insertions can be detected by a change in size of the amplified product in comparison to the normal genotype. Point mutations can be identified by hybridizing amplified DNA to radiolabeled HMF RNA or alternatively, radiolabeled HMF antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to an antigen to the polypeptide of the present invention, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein such as bovine serum albumen. Next, the monoclonal antibody is incubated in the dish during which time the monoclonal antibodies attach to any HMF proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of HMF protein present in a given volume of patient sample when compared against a standard curve.

A competition assay may be employed wherein antibodies specific to the polypeptide of the present invention are attached to a solid support and labeled HMF and a sample derived from the host are passed over the solid support and the amount of label detected attached to the solid support can be correlated to a quantity of HMF in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Expression and Purification of the Haemopoietic Maturation Factor

The DNA sequence encoding the polypeptide of the present invention, ATCC #75514, is initially amplified using PCR oligonucleotide primers corresponding to the 5' and 3' end of the DNA sequence to synthesize insertion fragments. The 5' oligonucleotide primer has the sequence

5'GACTTCATGAAAAAGACAGATATCGCAATTGCAGTGGCACTGGCTGGTTTCG    (SEQ ID NO:3)

CTACCGTTGCGCAAGCTGCTTCTGACTCCCTGGTGGTGTGC 3' contains a BspHI restriction enzyme site and the ompA leader sequence followed by 21 nucleotides of coding sequence starting from the codon following the methionine start codon; the 3' sequence 5'GACTAGATCTACGAAA-GAAAGACAAC TTTTC 3' (SEQ ID NO:4) contains complementary sequences to a BglII site, and the last 21 nucleotides of coding sequence. The restriction enzyme sites correspond to the restriction enzyme sites on the bacterial expression vector pQE-60 (Qiagen Inc., Chatsworth, Calif.). The plasmid vector encodes antibiotic resistance (Amp$^r$), a bacterial origin of replication (ori), an IPTG-regulatable promoter/operator (P/O), a ribosome binding site (RBS), a 6-histidine tag (6-His) and restriction enzyme cloning sites. The pQE-60 vector was digested with NcoI and BglII and the insertion fragments were then ligated into the pQE-60 vector maintaining the reading frame initiated at the bacterial RBS. The ligation mixture was then used to transform the E. coli strain m15/rep4 (Qiagen). M15/rep4 contains multiple copies of the plasmid pREP4, which expresses the lacd repressor and also confers kanamycin resistance (Kan$^r$). Transformants are identified by their ability to grow on LB plates containing both Amp and Kan. Clones containing the desired constructs were grown overnight (O/N) in liquid culture in either LB media supplemented with both Amp (100 µg/ml) and Kan (25 µg/ml). The O/N culture is used to inoculate a large culture at a ratio of 1:100 to 1:250. The cells were grown to an optical density of 600 (O.D. $^{600}$) between 0.4 and 0.6. IPTG ("Isopropyl-B-D-thiogalacto pyranoside") was then added to a final concentration of 1 mM. IPTG induces by inactivating the lacd repressor, clearing the P/O leading to increased gene expression. Cells were grown an extra 3–4 hours. Cells were then harvested by centrifugation. The cell pellet was solubilized in the chaotropic agent 6 Molar Guanidine HCL. After clarification, solubilized haemopoietic maturation factor was purified from this solution by chromatography on a Nickel-Chelate column under conditions that allow for tight binding by proteins containing the 6-His tag (Hochuli, E. et al., Genetic Engineering, Principle & Methods, 12:87–98 Plenum Press, New York (1990)). Haemopoietic maturation factor (95% pure) was eluted from the column in 6 molar guanidine HCL pH 5.0 and for the purpose of renaturation adjusted to 3 molar guanidine HCL, 100 mM sodium phosphate, 10 mmolar glutathione (reduced) and 2 mmolar gluthatione (oxidized). After incubation in this solution for 12 hours the protein was dialyzed to 50 mmolar sodium phosphate.

EXAMPLE 2
Haemopoietic Maturation Factor and Inhibition of Growth of HeLa Cells HeLa cells were plated at $10^5$ (experiment #1) or $10^4$ (experiment #2 and #3) per well in 24 well plates. Cells were grown in DMEM ("Dulbecco's Modified Eagle's Medium") medium (1 ml) containing 5% fetal calf serum, penicillin 50 units/ml and streptomycin 50 µg/ml. Four wells were plated for each concentration of the polypeptide of the present invention per experiment. Haemopoietic maturation factor was applied one day after plating. After 3 days cells were trypsinized and counted.

EXAMPLE 3
Expression of Recombinant Haemopoietic Maturation Factor in COBS Cells The expression of plasmid, pcHMF-HA is derived from a vector pcDNAI/Amp (Invitrogen) containing: 1) SV40 origin of replication, 2) ampicillin resistance gene, 3) E. coli replication origin, 4) CMV promoter followed by a polylinker region, an SV40 intron and polyadenylation site. A DNA fragment encoding the entire haemopoietic maturation factor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding haemopoietic maturation factor, ATCC #75514, was constructed by PCR on the original EST cloned using two primers: the 5' primer 5'GACTAAGCTTAGCCATGTCTGACTC-CCTGGTGGTG 3' (SEQ ID NO:5) contains a HindIII site followed by 21 nucleotides of haemopoietic maturation factor coding sequence starting from the initiation codon; the 3' sequence 5' GACTTCTAGATCAAGCG-TAGTCTGGGACGTCGTATGGGTAACGAAAGAAAGA CAACTTTTCTTG 3' (SEQ ID NO:6) contains complementary sequences to an XbaI site, translation stop codon, HA tag and the last 24 nucleotides of HMF coding sequence (not including the stop codon). Therefore, the PCR product contains a HindIII site, haemopoietic maturation factor coding sequence followed by HA tag fused in frame, a translation termination stop codon next to the HA tag, and an XbaI site. The PCR amplified DNA fragment and the vector, pcDNAI/Amp, were digested with HindIII and XbaI restriction enzyme and ligated. The ligation mixture was transformed into *E. coli* strain SURE (Stratagene Cloning Systems, La Jolla, Calif.) the transformed culture was plated on ampicillin media plates and resistant colonies were selected. Plasmid DNA was isolated from transformants and examined by restriction analysis for the presence of the correct fragment. For expression of the recombinant haemopoietic maturation factor, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the haemopoietic maturation factor HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Precipitated proteins were analyzed on 15% SDS-PAGE.

EXAMPLE 4
Cloning and Expression of Haemopoietic Maturation Factor Using the Baculovirus Expression System The DNA sequence encoding the full length haemopoietic maturation factor protein, ATCC #75514, was amplified using PCR oligonucleotide primers corresponding to the 5' and 3' sequences of the gene:

The 5' primer has the sequence CGCGGGATCCG-CATC<u>ATG</u>TCTGA CTCCCTGGTGG (SEQ ID NO:7) and contains a BamHI restriction enzyme site (in bold) followed by 6 nucleotides resembling an efficient signal for the initiation of translation in eukaryotic cells (Kozak, M., J. Mol. Biol., 196:947–950 (1987) which is just behind the first 79 nucleotides of the HMF gene (the initiation codon for translation "ATG" is underlined).

The 3' primer has the sequence 5' GCGCGGTAC-CAGTCCCCAGCCCAG AGATCA 3' (SEQ ID NO:8) and contains the cleavage site for the restriction endonuclease Asp718 and 20 nucleotides complementary to the 3' non-translated sequence of the haemopoietic maturation factor gene. The amplified sequences were isolated from a 1% agarose gel using a commercially available kit ("Geneclean," BIO 101 Inc., La Jolla, Calif.). The fragment was then digested with the endonucleases BamHI and Asp718 and then purified again on a 1% agarose gel. This fragment is designated F2.

The vector pRG1 (modification of pVL941 vector, discussed below) is used for the expression of the haemopoietic maturation factor protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp718. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and Asp718 and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E. coli* HB101 cells were then transformed and bacteria identified that contained the plasmid (pBacHMF) with the haemopoietic maturation factor gene using the enzymes BamHI and Asp718. The sequence of the cloned fragment was confirmed by DNA sequencing.

5 µg of the plasmid pBacHMF was co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBacHMF were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the virus was added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HMF at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours.

Expression media containing HMF was then diluted three fold to reduce the concentration of salts and then concentrated by membrane filtration to yield a solution that was one fifth of the starting material volume. The protein was then subjected to two anion exchange chromatography steps at pH 6.2 and pH 7.7. Analysis of the purified material showed essentially a single peak using reversed-phage HPLC (FIGS. 5A, B) and one band by SDS-PAGE analysis (FIG. 5C).

EXAMPLE 5
Expression of RNA Encoding Haemopoietic Maturation Factor in Human Monocytes The regulation of HMF mRNA in human monocytes was investigated by isolating total RNA from fresh elutriated monocytes treated with 100 U/ml hr rIFN-γ, 100 ng/ml LPS, or both stimuli simultaneously for various amounts of time. RNA (8 μg) from each treatment was separated electrophoretically on a 1.2% agarose gel and transferred to a nylon membrane. Haemopoietic maturation factor mRNA was quantified by probing the blot with $^{32}$P-labeled cDNA and the bands on the resulting autoradiograph were quantified densitometrically (FIG. 6).

Haemopoietic maturation factor is expressed constitutively in human monocytes at the mRNA level and gene expression is up-regulated in response to IFN-γ within 2 hrs. and LPS within 12 hrs., while the combination does not stimulate expression.

EXAMPLE 6
Stimulation of Haemopoietic Progenitor Cells by Baculovirus Expressed Haemopoietic Maturation Factor An in vitro colony formation assay was performed, where freshly isolated bone marrow cells are incubated in methylcellulose-containing culture medium for up to fourteen days in the presence or absence of any added factors. At days seven and fourteen, cultures are examined under an inverted light microscope to score for the number of colonies. In one set of experiments, mouse bone marrow cells were assayed for colony formation. As show in FIG. 7A growth medium obtained from cells producing the recombinant form of the HMF (Culture condition 3) stimulated the formation of the hematopoietic progenitor cell colonies that were associated with the bone marrow stromal cell colonies. In contrast, no significant number of colonies were detected when cells were cultured with either the assay medium alone (Culture condition 1) or in the presence of growth medium obtained from cells that were not producing HMF (Culture condition 2, negative control). In another assay, a partially purified preparation of HMF was tested against mouse (not shown) and human bone marrow cells. Data show in FIG. 7B demonstrate stimulation of hematopoietic colony formation in the presence of a partially purified preparation of HMF (Culture condition 3). No significant numbers of colonies were detected in the absence of any added factor (Culture condition 1) or in the presence of the column fraction not containing HMF (Culture condition 2, negative control). In addition, both mouse and human hematopoietic colonies produced in response to HMF contained cells representing the megakaryocyte, macrophage/monocyte, and granulocyte lineages, indicating that HMF is stimulating the proliferation and differentiation of multi-potential hematopoietic progenitor cells.

EXAMPLE 7
Effect of HMF on T-cell Proliferation

Normal peripheral blood T-cells were purified from whole blood in a two-step procedure using gradient centrifugation followed by passage over a T-cell enrichment column. From the purified T cells, CD4+ and CD8+ peripheral T-cell subsets were isolated by negative selection with a panning procedure using anti-CD8 and anti-CD 4 monoclonal antibodies, respectively. Total T cells, CD4+ and CD8+ cells were plated at 1×10(5) cells/well in 96-well plates in the presence of baculovirus-expressed, serial two-fold dilutions (quadruplicate samples for each dilution) of HPLC purified haemopoietic maturation factor protein of the invention. During the last 18–24 hours of a 3 day incubation at 37° C., the cells were pulsed with 1 μCi $^3$[H]-thymidine. Cells were harvested and lysed using a cell harvester, and the cpm incorporation was determined by liquid scintillation counting. Results are presented as the mean+/−sem of quadruplicate samples or the fold increase over background (See Table 1).

EXAMPLE 8
Effect of HMF on Thymic Cells

Thymic cell suspensions were obtained from the thymus of normal inbred rats. Thymocyte were plated at 1×10(5) cells/well in 96-well plates in the presence of baculovirus-expressed, serial two-fold dilutions (quadruplicate samples for each dilution) of HPLC purified haemopoietic maturation factor protein of the invention. During the last 18–24 hours of a 3 day incubation at 37° C., the cells were pulsed with 1 μCi $^3$[H]-thymidine. Cells were harvested and lysed using a cell harvester, and the cpm incorporation was determined by liquid scintillation counting. Results are presented as the mean+/−sem of quadruplicates samples or the fold increase over background (See Table 2).

EXAMPLE 9
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HimdIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. A method for stimulating the proliferation and differentiation of hematopoietic progenitor cells, comprising contacting bone marrow cells with an effective amount of a polypeptide selected from the group consisting of:
   (a) a polypeptide comprising residues 1 to 142 of SEQ ID NO:2;
   (b) a polypeptide comprising residues 2 to 142 of SEQ ID NO:2;
   (c) a polypeptide comprising the amino acid sequence of the polypeptide encoded by the human cDNA contained in ATCC® Deposit No. 75514; and
   (d) a polypeptide comprising the amino acid sequence of the mature polypeptide encoded by the human cDNA contained in ATCC® Deposit No. 75514.

2. The method of claim 1, wherein the polypeptide is (a).
3. The method of claim 2, wherein the polypeptide is administered to a patient suffering from leukemia.
4. The method of claim 2, wherein the polypeptide is administered to a patient suffering from a blood-related disorder.
5. The method of claim 1, wherein the polypeptide is (b).
6. The method of claim 5, wherein the polypeptide is administered to a patient suffering from leukemia.
7. The method of claim 5, wherein the polypeptide is administered to twat a patient suffering from a blood-related disorder.
8. The method of claim 1, wherein the polypeptide is (c).
9. The method of claim 8, wherein the polypeptide is administered to a patient suffering from leukemia.
10. The method of claim 8, wherein the polypeptide is administered to a patient suffering from a blood-related disorder.
11. The method of claim 1, wherein the polypeptide is (d).
12. The method of claim 11, wherein the polypeptide is administered to a patient suffering from leukemia.
13. The method of claim 11, wherein the polypeptide is administered to a patient suffering from a blood-related disorder.
14. A method for stimulating the proliferation of bone marrow stromal cells, comprising contacting said cells with an effective amount of a polypeptide selected from the group consisting of:
   (a) a polypeptide comprising residues 1 to 142 of SEQ ID NO: 2;
   (b) a polypeptide comprising residues 2 to 142 of SEQ ID NO: 2;
   (c) a polypeptide comprising the amino acid sequence of the polypeptide encoded by the human cDNA contained in ATCC® Deposit No. 75514; and
   (d) a polypeptide comprising the amino acid sequence of the mature polypeptide encoded by the human cDNA contained in ATCC® Deposit No. 75514.

15. The method of claim 14, wherein the polypeptide is (a).
16. The method of claim 14, wherein the polypeptide is (b).
17. The method of claim 1, wherein the polypeptide is (c).
18. The method of claim 1, wherein the polypeptide is (d).
19. A method for stimulating the proliferation and differentiation of CD4+ or CD8+ T-cells, comprising contacting T-cells with an effective amount of a polypeptide selected from the group consisting of:
   (a) a polypeptide comprising residues 1 to 142 of SEQ ID NO:2;
   (b) a polypeptide comprising residues 2 to 142 of SEQ ID NO:2;
   (c) a polypeptide comprising the amino acid sequence of the polypeptide encoded by the human cDNA contained in ATCC® Deposit No. 75514; and
   (d) a polypeptide comprising the amino acid sequence of the mature polypeptide encoded by the human cDNA contained in ATCC® Deposit No. 75514.

20. The method of claim 19, wherein the polypeptide is (a).
21. The method of claim 20, wherein the polypeptide is administered to a patient suffering from leukemia.
22. The method of claim 20, wherein the polypeptide is administered to a patient infected with HIV.
23. The method of claim 19, wherein the polypeptide is (b).
24. The method of claim 21, wherein the polypeptide is administered to a patient suffering from leukemia.
25. The method of claim 23, wherein the polypeptide is administered to a patient infected with HIV.
26. The method of claim 19, wherein the polypeptide is (c).
27. The method of claim 26, wherein the polypeptide is administered to a patient suffering from leukemia.
28. The method of claim 26, wherein the polypeptide is administered to a patient infected with HIV.
29. The method of claim 19, wherein the polypeptide is (d).
30. The method of claim 29, wherein the polypeptide is administered to a patient suffering from leukemia.
31. The method of claim 29, wherein the polypeptide is administered to a patient infected with HIV.
32. A method for stimulating the proliferation of thymocytes, comprising contacting said thymocytes with an effective amount of a polypeptide selected from the group consisting of:
   (a) a polypeptide comprising residues 1 to 142 of SEQ ID NO: 2;
   (b) a polypeptide comprising residues 2 to 142 of SEQ ID NO: 2;
   (c) a polypeptide comprising the amino acid sequence of the polypeptide encoded by the human cDNA contained in ATCC® Deposit No. 75514; and
   (d) a polypeptide comprising the amino acid sequence of the mature polypeptide encoded by the human cDNA contained in ATCC® Deposit No. 75514.

33. The method of claim 32, wherein the polypeptide is (a).
34. The method of claim 32, wherein the polypeptide is (b).
35. The method of claim 32, wherein the polypeptide is (c).
36. The method of claim 32, wherein the polypeptide is (d).
37. The method of claim 1, wherein said bone marrow cells are contacted with said polypeptide in vitro.
38. The method of claim 14, wherein said stromal cells are contacted with said polypeptide in vitro.
39. The method of claim 19, wherein said T-cells are contacted with said polypeptide in vitro.
40. The method of claim 32, wherein said thymocytes are contacted with said polypeptide in vitro.

* * * * *

UNITED STATES PATENT AND TRADEMARK OFFICE
CERTIFICATE OF CORRECTION

PATENT NO. : 6,790,826 B2
DATED : September 14, 2004
INVENTOR(S) : Kirkness et al.

It is certified that error appears in the above-identified patent and that said Letters Patent is hereby corrected as shown below:

Column 31,
Line 59, delete "The method of claim 1" and insert -- The method of claim 14 --;
Line 60, delete "The method of claim 1" and insert -- The method of claim 14 --;

Column 32,
Line 18, delete "The method of claim 21" and insert -- The method of claim 23 --.

Signed and Sealed this

Twenty-seventh Day of September, 2005

JON W. DUDAS
*Director of the United States Patent and Trademark Office*

SEQUENCE LISTING

<160> NUMBER OF SEQ ID NOS: 9

<210> SEQ ID NO 1
<211> LENGTH: 600
<212> TYPE: DNA
<213> ORGANISM: Homo sapiens
<220> FEATURE:
<221> NAME/KEY: CDS
<222> LOCATION: (46)..(474)
<223> OTHER INFORMATION:

<400> SEQUENCE: 1

```
agacagcgga actaagaaaa gaagaggcct gtggacagaa caatc atg tct gac tcc      57
                                                   Met Ser Asp Ser
                                                    1 ctg gtg gtg tgc gag gta gac cca gag cta aca gaa aag ctg agg aaa       105
Leu Val Val Cys Glu Val Asp Pro Glu Leu Thr Glu Lys Leu Arg Lys
  5                  10                  15                  20 ttc cgc ttc cga aaa gag aca gac aat gca gcc atc ata atg aag gtg       153
Phe Arg Phe Arg Lys Glu Thr Asp Asn Ala Ala Ile Ile Met Lys Val
                 25                  30                  35 gac aaa gac cgg cag atg gtg gtg ctg gag gaa gaa ttt cag aac att       201
Asp Lys Asp Arg Gln Met Val Val Leu Glu Glu Glu Phe Gln Asn Ile
             40                  45                  50 tcc cca gag gag ctc aaa atg gag ttg ccg gag aga cag ccc agg ttc       249
Ser Pro Glu Glu Leu Lys Met Glu Leu Pro Glu Arg Gln Pro Arg Phe
         55                  60                  65 gtg gtt tac agc tac aag tac gtg cat gac gat ggc cga gtg tcc tac       297
Val Val Tyr Ser Tyr Lys Tyr Val His Asp Asp Gly Arg Val Ser Tyr
     70                  75                  80 cct ttg tgt ttc atc ttc tcc agc cct gtg ggc tgc aag ccg gaa caa       345
Pro Leu Cys Phe Ile Phe Ser Ser Pro Val Gly Cys Lys Pro Glu Gln
 85                  90                  95                 100 cag atg atg tat gca ggg agt aaa aac agg ctg gtg cag aca gca gag       393
Gln Met Met Tyr Ala Gly Ser Lys Asn Arg Leu Val Gln Thr Ala Glu
                105                 110                 115 ctc aca aag gtg ttc gaa atc cgc acc act gat gac ctc act gag gcc       441
Leu Thr Lys Val Phe Glu Ile Arg Thr Thr Asp Asp Leu Thr Glu Ala
            120                 125                 130 tgg ctc caa gaa aag ttg tct ttc ttt cgt tga tctctgggct ggggactgaa     494
Trp Leu Gln Glu Lys Leu Ser Phe Phe Arg
        135                 140 ttcctgatgt ctgagtcctc aaggtgactg gggacttgga accctagga cctgaacaac      554 caagactta aataaatttt taaatgcaaa aaaaaaaaaa aaaaaa                     600
```

<210> SEQ ID NO 2
<211> LENGTH: 142
<212> TYPE: PRT
<213> ORGANISM: Homo sapiens

<400> SEQUENCE: 2

Met Ser Asp Ser Leu Val Val Cys Glu Val Asp Pro Glu Leu Thr Glu
1               5                   10                  15

Lys Leu Arg Lys Phe Arg Phe Arg Lys Glu Thr Asn Ala Ala Ile
            20                  25                  30

Ile Met Lys Val Asp Lys Asp Arg Gln Met Val Leu Glu Glu Glu
        35                  40                  45

Phe Gln Asn Ile Ser Pro Glu Glu Leu Lys Met Glu Leu Pro Glu Arg
    50                  55                  60

Gln Pro Arg Phe Val Val Tyr Ser Tyr Lys Tyr Val His Asp Asp Gly
65                  70                  75                  80

Arg Val Ser Tyr Pro Leu Cys Phe Ile Phe Ser Ser Pro Val Gly Cys
                85                  90                  95

Lys Pro Glu Gln Gln Met Met Tyr Ala Gly Ser Lys Asn Arg Leu Val
            100                 105                 110

Gln Thr Ala Glu Leu Thr Lys Val Phe Glu Ile Arg Thr Thr Asp Asp
        115                 120                 125

Leu Thr Glu Ala Trp Leu Gln Glu Lys Leu Ser Phe Phe Arg
    130                 135                 140

<210> SEQ ID NO 3
<211> LENGTH: 93
<212> TYPE: DNA
<213> ORGANISM: Artificial Sequence
<220> FEATURE:
<223> OTHER INFORMATION: Contains a BspHI restriction enzyme site and
      the ompA leader sequence.

<400> SEQUENCE: 3
gacttcatga aaaagacaga tatcgcaatt gcagtggcac tggctggttt cgctaccgtt      60
gcgcaagctg cttctgactc cctggtggtg tgc                                   93

<210> SEQ ID NO 4
<211> LENGTH: 31
<212> TYPE: DNA
<213> ORGANISM: Artificial Sequence
<220> FEATURE:
<223> OTHER INFORMATION: Contains complementary sequences to a BglII
      site.

<400> SEQUENCE: 4
gactagatct acgaaagaaa gacaactttt c                                     31

<210> SEQ ID NO 5
<211> LENGTH: 35
<212> TYPE: DNA
<213> ORGANISM: Artificial Sequence
<220> FEATURE:
<223> OTHER INFORMATION: Contains a HindIII site.

<400> SEQUENCE: 5
gactaagctt agccatgtct gactccctgg tggtg                                 35

<210> SEQ ID NO 6
<211> LENGTH: 64
<212> TYPE: DNA

```
<213> ORGANISM: Artificial Sequence
<220> FEATURE:
<223> OTHER INFORMATION: Contains complementary sequences to an XbaI
      site, translation stop codon, and an HA tag.

<400> SEQUENCE: 6
gacttctaga tcaagcgtag tctgggacgt cgtatgggta acgaaagaaa gacaactttt    60
cttg                                                                 64

<210> SEQ ID NO 7
<211> LENGTH: 35
<212> TYPE: DNA
<213> ORGANISM: Artificial Sequence
<220> FEATURE:
<223> OTHER INFORMATION: Contains a BamHI restriction enzyme site
      followed by 6 nucleotides resembling an efficient signal for
      the initiation of translation in eukaryotic cells
      (Kozak, M., J. Mol. Biol., 196:947-950 (1987).

<400> SEQUENCE: 7
cgcgggatcc gccatcatgt ctgactccct ggtgg                               35

<210> SEQ ID NO 8
<211> LENGTH: 30
<212> TYPE: DNA
<213> ORGANISM: Artificial Sequence
<220> FEATURE:
<223> OTHER INFORMATION: Contains the cleavage site for the restriction
      endonuclease Asp718.

<400> SEQUENCE: 8
gcgcggtacc agtccccagc ccagagatca                                     30

<210> SEQ ID NO 9
<211> LENGTH: 141
<212> TYPE: PRT
<213> ORGANISM: Homo sapiens

<400> SEQUENCE: 9

Met Ser Glu Ser Leu Val Val Cys Asp Val Ala Glu Asp Leu Val Glu
1               5                   10                  15

Lys Leu Arg Lys Phe Arg Phe Arg Lys Glu Thr Asn Asn Ala Ala Ile
            20                  25                  30

Ile Met Lys Ile Asp Lys Asp Lys Arg Leu Val Val Leu Asp Glu Glu
        35                  40                  45

Leu Glu Gly Ile Ser Pro Asp Glu Leu Lys Asp Glu Leu Pro Glu Arg
    50                  55                  60

Gln Pro Arg Phe Ile Val Tyr Ser Tyr Lys Tyr Gln His Asp Asp Gly
65                  70                  75                  80

Arg Val Ser Tyr Pro Leu Cys Phe Ile Phe Ser Ser Pro Val Gly Cys
                85                  90                  95

Lys Pro Glu Gln Gln Met Met Tyr Ala Glu Ser Lys Asn Lys Leu Val
            100                 105                 110

Gln Thr Ala Glu Leu Thr Lys Val Phe Glu Ile Arg Asn Thr Glu Asp
        115                 120                 125

Leu Thr Glu Glu Trp Leu Arg Glu Lys Leu Gly Phe Phe
    130                 135                 140
```